United States Patent

Behrendt et al.

[11] 4,025,633
[45] May 24, 1977

[54] α,α-DIARYL-β-(TERT-AMINO)-PROPANOLS AND PHARMACEUTICAL COMPOSITIONS CONTAINING THEM

[75] Inventors: Wilhelm A. Behrendt, Niederweimar, Kreis Marburg; Bernhard Stieh, Marburg, both of Germany

[73] Assignee: Firma Temmler A.G., Basel, Switzerland

[22] Filed: Mar. 3, 1975

[21] Appl. No.: 554,902

[30] Foreign Application Priority Data

Mar. 4, 1974 Germany .......................... 2410284

[52] U.S. Cl. .......................... 424/267; 260/293.58; 260/293.83; 260/293.84; 260/326.5 R; 424/274

[51] Int. Cl.$^2$ ..................................... C07D 405/06

[58] Field of Search ................. 260/293.58, 293.83, 260/293.84, 326.5 R; 424/267, 274

[56] References Cited

UNITED STATES PATENTS

| | | | |
|---|---|---|---|
| 2,827,460 | 3/1958 | Stein et al. | 260/247.7 |
| 3,190,920 | 6/1965 | Spickett et al. | 260/570 |

*Primary Examiner*—G. Thomas Todd

*Attorney, Agent, or Firm*—Toren, McGeady and Stanger

[57] ABSTRACT

α,α-Diaryl-β-(tert-amino)-propanols having the general formula:

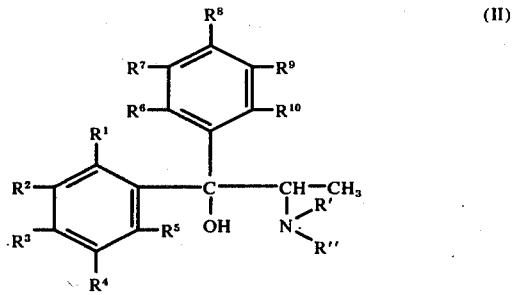

wherein R', R'' and $R^1$ to $R^{10}$ represent certain specific substituent groups, exhibit a diuretic and saluretic activity.

Pharmaceutical composition containing at least one compound of the general Formula II together with a pharmaceutically acceptable diluent or carrier. The pharmaceutical compositions may be in a form suitable for oral or parenteral administration.

4 Claims, No Drawings

α,α-DIARYL-β-(TERT-AMINO)-PROPANOLS AND PHARMACEUTICAL COMPOSITIONS CONTAINING THEM

BACKGROUND OF THE INVENTION

The present invention relates to derivatives of α,α-diaryl-β-(tert-amino)-propanols, processes for their preparation, and also to pharmaceutical compositions containing them.

PRIOR ART

α,α-Diaryl-β-(tert-amino)-propanols of the general formula:

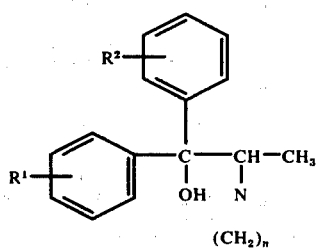

(I)

are known, wherein $R^1$ and $R^2$ are each independently a halogen atom, an oxybenzyl radical, a lower alkyl or a lower alkoxy group and $-N(CH_2)_n$ is a saturated N-heterocyclic radical, which is connected via the ring-stable nitrogen atom. These compounds possess antitussive activity. The compounds of formula (I) may be prepared in known manner by the reaction of (α-dialkyl amino-ethyl)aryl ketones with aryl magnesium halides.

SUMMARY OF THE INVENTION

Surprisingly, compounds of the α,α-diaryl-β-(tert-amino)-propanols having saluretic activity have now been found.

Accordingly, the present invention provides α,α-diaryl-β-(tert-amino)-propanols of the general formula:

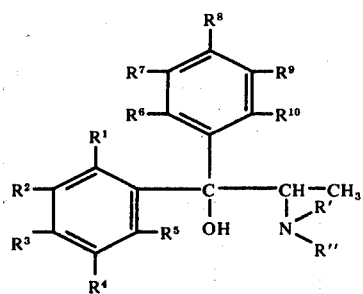

(II)

in which R' and R" are each independently a straight or branched chain lower alkyl group having from 1 to 6 carbon atoms, or R' and R" together with the nitrogen atom, form a 5- or 6-membered ring, and $R^1$ to $R^{10}$ are each independently a hydrogen or halogen atom, a straight or branched chain alkyl group having from 1 to 6 carbon atoms, an alkenyl group having 2 or 3 carbon atoms, a hydroxy group, a lower alkoxy group having from 1 to 4 carbon atoms, an oxybenzyl group or wherein two adjacent substituents together form a 5- or 6-membered heterocyclic ring having one or two hetero-atoms.

DESCRIPTION OF PREFERRED EMBODIMENTS

These multiple-substituted α,α-diaryl-β-(tert-amino)-propanols of the formula (II) exhibit a diuretic and saluretic effect which differs from that of diuretics found commercially.

Medicaments which result in an increased discharge of urine and produce an increased elimination of sodium and chlorine ions via the kidneys (saluretics) are used for example in the treatment of oedema, in widely varying convalescent conditions and in the therapy of high-pressure conditions.

In addition to eliminating sodium and chloride, saluretics normally also effect at the same time an increase in the excretion of potassium. Such an effect is disadvantageous, since it carries with it the risk, particularly in long-term therapy, of a potassium-depletion of the organism.

Diuretics, in which this side effect is not found, are of particular interest. They are classified pharmacologically as aldosterone-antagonists or as pseudo-antialdosterones or anti-kaliuretic diuretics. Previously known examples of medicaments of this type are the aldosterone antagonist 7α-acetylthio-3-oxo-4-androsten-17-spiro-2'-tetrahydrofurane-5'-one which is from the group of the spironolactones and the antikaliuretic diuretics 2.4.7-triamono-6-phenyl-pteridine and N-amidino-3.5-diamino-6-chloropyrazinocarboxamide.

However in patients, in which sodium is retained, these compounds generally only have a slight effect on the sodium elimination. For this reason they are generally only used in combination with a powerful saluretic. This procedure involves disadvantages since the effect of such a combination is frequently quantitatively impossible to anticipate. The effect will depend on the relationship between the primary disease and the simultaneous administration of the saluretic and anti-keliuretic diuretic, and furthermore gives rise to problems in respect of the possible concurrence of side effects. Furthermore, the previously known anti-kaliuretics may cause potassium congestion in the body, since because of their anti-kaliuretic action potassium is retained in the organism, if its elimination via the kidneys is not increased.

For these reasons, new diuretics have been sought which possess both anti-kaliuretic and saluretic activity.

As can be seen from the results of pharmacological tests which are summarised in the following tables, the compounds of the present invention increase the water and sodium chloride elimination beyond that obtained with 2.4.7-triamino-6-phenyl-pteridine, without inhibiting the elimination of potassium, and furthermore do not increase the excretion of potassium, such as is known with the conventional saluretics. It can be seen from Table 2 that the potassium values obtained using the compounds of the invention, by contrast with the reference compositions, are in the range which is considered to be normal.

It is also found that the novel compounds not only possess more favourable properties than 2.4.7-triamino-6-phenyl-pteridine, but that they to some extent also considerably surpass the effect of 6-chloro-3.4-dihydro-7-sulpho-amoyl-2H-1.2.4-benzodiazine-1.1-dioxide with respect to their diuretic and saluretic action. The following explanations are given with regard to the tables.

In order to test the saluretic efficiency of the compounds of the invention rats having a weight of 150 to 200g were used. The animals were kept without food, but not without drinking water, for 15 hours before the beginning of the test. The test substances were administered to groups of four rats, of substantially equal weight, with a rigid stomach probe in a 1% methyl cellulose slime. The dose required per 100g animal (unit dosage in $\mu$mol/kg body weight) was contained in one ml. Following the administration of the substance the rats were given 5 ml 0.9% sodium chloride solution per 100g body weight p.o. and placed in a diuresis funnel after manually emptying the bladder. Urine was collected for 6 hours in an air-conditioned chamber at 24° ± 1° C and a relative air humidity of 50 ± 5%. The diuretic effect of a particular dose was tested on at least two, but more frequently however on four to eight groups of rats. Two sodium chloride controls were also used for each test day.

At the end of the collecting periods the volumes of urine discharged per group were noted and the pH value and also the content of sodium, potassium (flame-photometrically) and chloride (measured argentometrically with the determination of the end point potentiometrically) were determined.

From the analysis results the quantities of $Na^+$, $K^+$ and $Cl^-$ eliminated were calculated in mol/lg body weight, and the values thus obtained compared with those of the control animals.

Means values and twice the standard deviation were calculated from the data for the sodium chloride controls, in order to determine the normal range. Then, for the values found with the test substances, the percentage variations from the average in respect of these parameters were calculated and tabulated. In this connection, with the results given in Table 1, the upper limit of the normal range, which is defined as the mean value plus twice the standard deviation, was selected as the reference quantity for the variations. In this way relevant hyper-eliminations could clearly be recognised.

In Table 2, the mean percentage variations in potassium elimination after administration of the compounds in accordance with the invention are compared with the mean value of the potassium elimination in the case of the sodium chloride controls. At the same time the Ma/K ratio is given which provides conclusive evidence of the effective saluretic property. The larger this quotient is, then the more sodium than potassium is eliminated in proportion.

Table 1

| | Influence on the elimination of water and sodium chloride | | |
|---|---|---|---|
| Substance | Dose $\mu$mol/kg body wt. oral | Mean percentage variation in the elimination[1] | | |
| | | H$_2$O | Sodium | Chloride |
| T 1523 | 40 | 28.9 | 13.1 | −5.1 |
| | 80 | 39.6 | 28.2 | 14.2 |
| T 1856 | 40 | 41.0 | 30.6 | 19.4 |
| | 80 | 59.7 | 47.6 | 32.5 |
| T 1857 | 40 | 52.0 | 54.8 | 32.9 |
| | 80 | 56.5 | 54.6 | 36.0 |
| T 1882 | 40 | 17.7 | 24.4 | 6.3 |
| | 80 | 7.5 | 9.5 | −4.4 |
| T 2111 | 40 | 36.8 | 33.5 | 9.5 |
| | 80 | 33.8 | 37.1 | 23.4 |
| T 2129 | 40 | 23.9 | 32.6 | 12.4 |
| | 80 | 21.3 | 19.4 | 22.0 |
| T 2152 | 40 | 22.9 | 22.7 | 11.6 |
| | 80 | 22.6 | 20.4 | 5.6 |
| T 2237 | 40 | 40.8 | 32.1 | 24.3 |
| | 80 | 67.9 | 59.8 | 57.1 |
| T 2258 | 40 | 28.1 | 22.9 | 12.8 |

Table 1-continued

| | Influence on the elimination of water and sodium chloride | | |
|---|---|---|---|
| Substance | Dose $\mu$mol/kg body wt. oral | Mean percentage variation in the elimination[1] | | |
| | | H$_2$O | Sodium | Chloride |
| | 80 | 32.3 | 24.6 | 17.3 |
| T 2259 | 40 | 46.5 | 28.7 | 94.0 |
| | 80 | 76.6 | 59.8 | 109.7 |
| T 2266 | 40 | −12.9 | −7.7 | −13.2 |
| | 80 | 19.7 | 19.4 | 12.2 |
| T 2310 | 40 | 41.3 | 27.3 | 8.9 |
| | 80 | 67.9 | 42.3 | 36.3 |
| T 2350 | 40 | 24.1 | 5.5 | 2.6 |
| | 80 | 49.8 | 40.5 | 21.2 |
| 2.4.7-triamino-6-phenyl-pteridine | 40 | −1.0 | −4.0 | −11.7 |
| | 80 | −2.0 | −0.2 | −11.7 |
| T 2378 | 40 | 6.7 | 6.7 | −5.6 |
| | 80 | 39.6 | 45.0 | −20.4 |
| T 2453 | 40 | 13.4 | 7.6 | 6.9 |
| | 80 | 51.7 | 62.2 | 31.2 |
| T 2455 | 40 | 39.8 | 31.3 | 21.4 |
| | 80 | 62.4 | 55.8 | 34.8 |
| T 2458 | 40 | 30.9 | 40.4 | 16.9 |
| | 80 | 83.8 | 84.2 | 59.0 |
| T 2464 | 40 | 49.8 | 64.4 | 30.4 |
| | 80 | 65.9 | 79.0 | 38.3 |
| T 2481 | 40 | 3.0 | −2.4 | −7.5 |
| | 80 | 34.1 | 43.8 | 20.0 |
| T 2493 | 40 | 59.2 | 62.7 | 41.0 |
| | 80 | 64.4 | 76.8 | 41.5 |

6-chloro-3.4.-dihydro-7-sulphamoyl-2H-1.2.4.-benzothiadiazine-1.1.-dioxide, a typical saluretic, produced with a dose of 10 mol/kg body weight a maximum hyper-elimination amounting on an average for water to 19.9%, sodium 29.6% and chloride 17.3%.

FOOTNOTES

[1] Deviations from the limits, defined by the average plus twice the standard deviation (X + 2S), of the control tests.

[2] Negative prefixes indicate that there is no hyper-elimination by comparison with the sodium chloride controls.

Table 2

| | Influence on the elimination of potassium | | |
|---|---|---|---|
| Substance | Dose $\mu$mol/kg body wt. oral | Mean percentage variation in the elimination of potassium[1] | Quotient Na/K |
| T 1523 | 40 | 25.5 | 5.35 |
| | 80 | 13.3 | 6.72 |
| T 1856 | 40 | 25.5 | 6.18 |
| | 80 | 22.4 | 7.16 |
| T 1857 | 40 | 30.6 | 7.04 |
| | 80 | 29.6 | 7.09 |
| T 1882 | 40 | 13.3 | 6.52 |
| | 80 | −12.2 | 7.41 |
| T 2111 | 40 | 19.4 | 6.64 |
| | 80 | −7.1 | 8.77 |
| T 2129 | 40 | 12.3 | 7.02 |
| | 80 | 35.7 | 5.23 |
| T 2152 | 40 | 9.2 | 6.67 |
| | 80 | 9.2 | 6.55 |
| T 2237 | 40 | 13.3 | 6.93 |
| | 80 | 19.4 | 7.95 |
| T 2258 | 40 | 19.4 | 6.11 |
| | 80 | 1.0 | 7.32 |
| T 2259 | 40 | 19.4 | 6.40 |
| | 80 | 38.8 | 6.84 |
| T 2266 | 40 | −2.0 | 5.59 |
| | 80 | 4.0 | 6.81 |
| T 2310 | 40 | 14.3 | 6.62 |
| | 80 | −2.0 | 8.64 |
| T 2350 | 40 | −2.0 | 7.00 |
| | 80 | 25.5 | 6.65 |
| 2.4.7.-triamino-6-phenyl-pteridine | 40 | −43.9(*) | 10.16(**) |
| | 80 | −55.1(*) | 13.20(**) |
| T 2378 | 40 | 11.2 | 5.70 |
| | 80 | 32.7 | 6.49 |
| T 2453 | 40 | −2.0 | 6.52 |
| | 80 | ±0 | 9.63 |
| T 2455 | 40 | 13.3 | 6.88 |
| | 80 | −23.5 | 12.93 |
| T 2458 | 40 | 49.0+ | 5.60 |
| | 80 | 37.7 | 8.06 |
| T 2464 | 40 | 9.2 | 8.94 |
| | 80 | −1.0 | 10.74 |
| T 2481 | 40 | −4.1 | 6.04 |

Table 2-continued

| | Influence on the elimination of potassium | | |
|---|---|---|---|
| Substance | Dose μmol/kg body wt. oral | Mean percentage variation in the elimination of potassium[1] | Quotient Na/K |
| T 2493 | 80 | 16.3 | 7.34 |
| | 40 | 35.7 | 7.74 |
| | 80 | 34.7 | 7.88 |

With the maximum effective dose of 6-chloro-3.4.dihydro-7-sulamoyl-2H-1.2.4-benzodiazine-1.1-dioxide (10 mol/kg body wt.) in the case of potassium an hyper-elimination of 58.3% (*) was recorded. The Na/K ratio of the quantities eliminated was 4.86.
FOOTNOTES
(*)Value lies outside the normal range.
(**)This extraordinarily high quotient can be explained in that the elimination of sodium remained unaffected while that of potassium was markedly reduced.
[1]In relation to the mean value of the K+ elimination of the controls.
[2]Negative prefixes indicate that there is no hyper-elimination in comparison with the sodium chloride controls.

Furthermore, the compounds in accordance with the invention differ advantageously from the hitherto known anti-kaliuretic diuretics with respect to their toxicity.

In Table 3 the mean lethal doses for mice, administered orally (LD$_{50}$ determination by the LICHTFIEL & WILCOXON method — J. Pharmacol. Exp. Ther. 96,99 (1949)) are compared.

Table 3

| | Comparison of toxicity in mice |
|---|---|
| Substance | LD$_{50}$ mg/kg body Wt. oral, observation period 7 days, 95% confidence limit in brackets |
| T 1523 | >3200 |
| T 1856 | 2200 (1209 – 4004) |
| T 1857 | 3825 (2675 – 5470) |
| T 1882 | 3400 (2656 – 4352) |
| T 2111 | 4450 (3560 – 5563) |
| T 2129 | >3200 |
| T 2152 | |
| T 2237 | > 6400 |
| T 2258 | > 4500 |
| T 2259 | 560 (444 – 706) |
| T 2266 | > 3200 |
| T 2310 | 520 (361 – 749) |
| T 2350 | > 4500 |
| 2.4.7-triamino-6-phenyl-pteridine | ca. 300[1] |
| N-Amidino-3.5-di-amino-6-chloro-pyrazin-carboxamid | 70[2] |
| T 2378 | 1600 |
| T 2453 | 700 (569 – 841) |
| T 2455 | 4550 |
| T 2458 | 3200 |
| T 2464 | > 4550 |
| T 2481 | 3775 (3341 – 4266) |
| T 2493 | 3610 (2597 – 5018) |

[1]CLARKE, D: Identification of Drugs, p. 581, London, Pharmaceutical Press, 1971
[2]ERHARD, G. and H. RUSCPIC (Hsg): Arzneimittel 2nd edn. Vol. 2, p. 351 Weinheim/Bergstr., Verlag Chemie. 1972.

The compounds of the present invention may be used in pharmaceutical compositions both in the free form and in the form of their salts. They may be administered orally or parenterally, in admixture with the usual pharmaceutical diluents or carriers used in human or veterinary medicine.

The carrier may be one or more inorganic or organic substance which are suitable for parenteral or oral administration and which do not react with the compounds of the invention. Examples of suitable carriers are water, vegetable oils, polyethylene glycols, gelatin, lactose, starch, magnesium stearate and talc.

For parenteral administration the compositions may be used in the form of aqueous or oily solutions, suspensions, emulsions, implants or suppositories.

For oral administration tablets or dragees may also be used.

The new compounds listed below are compounds in accordance with the invention.

1) 1-(4'Methoxy-2'methyl-5'-isopropylphenyl)-1-phenyl-2-piperidino-propan-1-ol.
2) 1-(4'-Methoxy-2'-methyl-5'-tert-butylphenyl)-1-phenyl-2-pyrrolidino-propan-1-ol.
3) 1-(2'-Methoxy-3'-methyl-5'-tert-butylphenyl)-1-phenyl-2-piperidino-propan-1-ol.
4) 1-(4'Methoxy-3',5'-diisopropylphenyl)-1-(3'',4''-dimethoxyphenyl)-2-piperidino-propan-1-ol.
5) 1-(2'-Methoxy-3'-methy-5'-tert-hexylphenyl)-1-phenyl-2-pyrrolidino-propan-1-ol.
6) 1-(7',8'-Dimethylchromanyl-(6'))-1-phenyl-2-piperidino-propan-1-ol.
7) 1-(4'-Methoxy-2',3',5',6'-tetramethylphenyl)-1-phenyl-2-piperidino-propan-1-ol.
8) 1-(4'-Methoxy-3',5'-diisopropylphenyl)-1-(4''-methoxyphenyl)2-piperidino-propan-1-ol.
9) 1-(4'-Methoxy-3',5'-diisopropylphenyl)-1-(4''-ethoxyphenyl)-2-piperidino-propan-1-ol.
10) 1-(2'-Methoxy-5'-tert-butylphenyl)-1-phenyl-2-piperidino-propan-1-ol.
11) 1-(4'Methoxy-3',5'-diisopropyl-phenyl)-1-(4''-methoxy-3'', 5''-dimethylphenyl)-2-piperidino-propan-1-ol.
12) 1-(4'-Ethoxy-3',5'-diisopropylphenyl)-1-(4''-methoxyphenyl)-2-piperidino-propan-1-ol.
13) 1-(3'-Chloro-6'-methoxy-2'methyl-5'-isopropyl-phenyl)-1-phenyl-2-pyrrolidino-propan-1-ol.
14) 1-(4'-Ethoxy-3',5'-diisopropylphenyl)-1-(4''-methoxyphenyl)-2-piperidino-propan-1-ol.
15) 1-(3'-Chloro-6'-methoxy-2'-methyl-5'-isopropyl-phenyl)-1-phenyl-2-pyrrolidino-propan-1-ol.
16) 1-(3',4'-Methylene-dioxy-6'-allylphenyl)-1-(4''-methoxyphenyl)-2-piperidino-propan-1-ol.
17) 1-(4'-Ethoxy-3',5'-diisopropylphenyl)-1-(4''-ethoxyphenyl)-2-piperidino-propan-1-ol.
18) 1-(2'-Methoxy-3'-methyl-5'-tert-butylphenyl)-1-(2'',4''-dimethoxyphenyl)-2-piperidino-propan-1-ol.
19) 1-(2'-Methoxy-3'-methyl-5'-tert-butylphenyl)-1-(2''-(or 4'') hydroxy-4'' (or 2'')-methoxyphenyl)-2-piperidino-propan-1-ol.
20) 1-(2'-Methoxy-3'-methyl-5'-tert-butylphenyl)-1-(3'',4''-dimethoxyphenyl)-2-piperidino-propan-1-ol.

The present invention also includes within its scope a process for the preparation of a compound of Formula (II) as hereinbefore defined which comprises dissolving in diethyl ether a) α-piperidinopropiophenone or a derivative thereof,
b) α-pyrrolidinopropiophenone or a derivative thereof or
c) a piperidinopropan-1-one derivative, adding the said solution of (a), (b) or (c) to a Grignard solution of magnesium and d) a halogenated, alkylated anisole compound,
e) a halogenated dialkylchromane,
f) a halogenated alkyl-phenetol,
g) a bromobenzene derivative or
h) a halogenated thymolmethylether, 1,2-dibromoethane and diethyl ether, boiling the mixture under reflux and treating the reaction mixture so obtained by pouring it onto ice, acidifying with hydrochloric acid, and either i) recovering the crystals precipitated therefrom, or j) separating the aqueous solution and the oily intermediate layer making these layers alkaline, and recovering the base which separates therefrom.

The following Examples illustrate the preparation of compounds in accordance with the invention.

EXAMPLE 1 (T 1523)

26 g of α-piperidinopropiophenone were added to a Grignard solution of 4 g of magnesium and 40 g of 4-bromothymolmethylether in 200 ml of diethyl ether. After boiling for 4 hours under reflux, the reaction mixture was poured on to ice, immediately acidified with hydrochloric acid and the crystals precipitated from the mixture were filtered off by suction. The crystals were then washed with diethyl ether and were added, while still moist, to a mixture of concentrated ammonia solution and petroleum ether. After brief agitation, the crystals dissolved. The petroleum ether extract was separated, dried with potash and then the petroleum ether was removed by evaporation. 23.7 g of 1-(4'-methoxy-2'-methyl-5'-isopropylphenyl)-1-phenyl-2-piperidino-propan-1-ol, having a melting point of 134° C to 135° C were obtained.

EXAMPLE 2 (T 1856)

22 g of α-pyrrolidinopropiophenone were added to a Grignard solution of 7.3 g of magnesium, 38.5 g of 4-bromo-5-methyl-2-tert-butylanisole and 28.2 g of 1,2-dibromoethane in 300 ml of diethyl ether. After boiling for 4 hours under reflux, the reaction mixture was poured onto ice and acidified with hydrochloric acid. The crystals which precipitated from the water-ether mixture were filtered off by suction, washed with diethyl ether and added to a mixture of concentrated ammonia solution with diethyl ether. After brief agitation the crystals dissolved. The ether extract was separated, dried with potash and the ether was removed by evaporation. The remaining viscous brown oil was dissolved in a little isopropanol. After a short time, 28.2 g of 1-(4'-methoxy-2'-methyl-5'-tert-butylphenyl)-1-phenyl-2-pyrrolidino-propan-1-ol, having a melting point of 112° C to 113° C, crystallized out. This product was recrystallized from isopropanol and then had a melting point of 113° C to 114° C.

EXAMPLE 3 (T 1857)

15 g of α-piperidinopropiophenone were added to a Grignard solution of 7.3 g of magnesium, 38.5 g of 6-bromo-2-methyl-4-tert-butylanisole and 28.2 g of 1,2,-dibromethane in 300 ml of diethyl ether. After boiling for 4 hours under reflux, the reaction mixture was poured on to ice and acidified with hydrochloric acid. The acidic aqueous solution and the oily intermediate layer were both separated, together made alkaline with a concentrated aqueous ammonia solution, and the base which separated therefrom was dissolved in diethyl ether. After evaporation of the diethyl ether, 26.5 g of a viscous brown oil were obtained from which, upon trituration of dilution with isopropanol, 21.5 g of 1-(2'-methoxy-3'-methyl-5'-tert-butylphenyl)-1-phenyl-2-piperidino-propan-1-ol, having a melting point of 86° C to 87° C, crystallized out. The product was recrystallized from isopropanol and then had a melting point of 87° C to 88° C.

EXAMPLE 4 (T 1882)

12 g of 1-(3',4'-dimethoxyphenyl)-2-piperidino-propan-1-one were added to a Grignard solution of 7.3 g of magnesium, 40.6 g of 4-bromo-2,6-diisopropylanisole and 28.2 g of 1,2-dibromoethane in 300 ml of diethyl ether. After boiling for 4 hours under reflux, the reaction mixture was poured onto ice and acidified with hydrochloric acid. The acidic aqueous solution and the oily intermediate layer were both separated, together made alkaline with a concentrated aqueous ammonia solution and the base which precipitated therefrom was dissolved in diethyl ether. After drying the diethyl ether extract over potash and evaporation of the diethyl ether, 24.7g of a yellowish-brown oil were obtained. On dilution with isopropanol, 14.8 g of crude 1-(methoxy-3',5'-diisopropylphenyl)-1-(3'',4''-dimethoxyphenyl)-2-piperidino-propan-1-ol, having a melting point of 118° C to 119° C crystallised out. After recrystallization from isopropanol the pure compound melted at 120° to 121° C.

EXAMPLE 5 (T2111)

7.5 g α-pyrrolidinopropiophenone were added to a Grignard solution, of 3.6 g of magnesium, 21.5 g of 2-methyl-4-tertiary-hexyl-6-bromoanisole, 14.1 g of 1,2-dibromoethane and 200 ml of diethyl ether. After boiling for 4 hours under reflux, the reaction mixture was poured onto ice and acidified with hydrochloric acid. The acidic aqueous solution and the oil intermediate layer were both separated, together made alkaline with a concentrated aqueous ammonia solution and the base which precipitated therefrom was dissolved in diethyl ether. After drying the diethyl ether extract over potash and evaporation of the diethyl ether, 14.8 g of a brown oil were obtained. On dilution with isopropanol, 8.3 g of crude 1-(2'-methoxy-3'-methyl-5'-tertiary-hexylphenyl)-1-phenyl-2-pyrrolidino-propan-1-ol, having a melting point of 96° C to 97° C, were obtained. After recrystallization from isopropanol the compound melted at 97° C to 98° C.

EXAMPLE 6 (T 2129)

15 g of α-piperidinopropiophenone in 20 ml of ether were added to a Grignard solution of 5.4 g of magnesium, 26.5 g of 6-bromo-7.8-dimethylchromane and 20.7 g of 1,2-dibromoethane in 80 ml diethyl ether. After boiling for 4 hours under reflux, the reaction mixture was poured onto ice and acidified with hydrochloric acid. The crystals which precipitated from the mixture were filtered by suction. The crystals were mixed, while still moist, with a concentrated aqueous ammonia solution and the mixture was extracted with diethyl ether several times. After drying the combined diethyl ether extracts over potash and evaporation of the diethyl ether, an oil was obtained which crystallized out after a short time. After recrystallization from methanol 5.2 g of pure 1-(7',8'-dimethylchromoanyl-(6'))-1-phenyl-2-piperidino-propan-1-ol, having a melting point of 125° C to 128° C were obtained.

EXAMPLE 7 (T 2152)

18.0 g of α-piperidinopropiophenone were added to a Grignard solution of 7.3 g magnesium, 36.4 g of 4-bromo-2,3,5,6-tetramethylanisole, 28.2 g of 1,2-dibromoethane and 300 ml of diethyl ether. After boiling for 4 hours under reflux, the reaction mixture was poured onto ice and acidified with hydrochloric acid. The acidic aqueous solution and the oily intermediate layer were both separated, together made alkaline with a concentrated aqueous ammonia solution and the base which precipitated therefrom was disolved in ether.

After evaporation of the diethyl ether, a brown oil was obtained. On dilution with methanol, 10.5 g of 1-(4'-methoxy-2',3',5',6'-tetramethylphenyl)-1-phenyl-2-piperidino-propan-1-ol, having a melting point of 148° C to 150° C, were obtained. After recrystallization from isopropanol, the pure compound melted at 151° C to 152° C.

EXAMPLE 8 (T 2237)

10 g of p-methoxy-α-piperidino-propiophenone were added to a Grignard solution of 4.8 g of magnesium, 27.1 g of 4-bromo-2,6-diisopropylanisole, 18.8 g of 1,2-dibromoethane and 200 ml of diethyl ether. After boiling for 4 hours under reflux, the reaction mixture was poured onto ice and acidified with hydrochloric acid. The aqueous acidic solution and the oily intermediate layer were both separated, together made alkaline with concentrated aqueous ammonia solution and the base which separated therefrom was dissolved in diethyl ether. After evaporation of the diethyl ether, 18.2 g of a brown oil were obtained. On dilution with methanol 12.9 g of 1-(4'-methoxy-3',5'-diisopropylphenyl)-1-(4''-methoxyphenyl)-2-piperidino-propan-1-ol, having a melting point of 62° to 64° C, were obtained. After recrystallization the pure compound melted at 64° C to 65° C.

EXAMPLE 9 (T 2258)

8 g of p-ethoxy-α-piperidino-propiophenone were added to a Grignard solution of 4.8 g of magnesium, 27.1 g of 4-bromo-2,6-diisopropylanisole, 18.8 g of 1,2-dibromoethane and 200 ml of diethyl ether. After boiling for 4 hours under reflux, the mixture was poured onto ice and acidified with hydrochloric acid. The aqueous acidic layer and the oily intermediate layer, were both separated together made alkaline with a concentrated aqueous ammonia solution and extracted with diethyl ether several times. The combined diethyl ether extracts were dried over potash, the diethyl ether was evaporated therefore and the residue was diluted with isopropanol. The resultant crude crystalline 1-(4'-methoxy-3',5'-diisopropylphenyl)-1-(4''-ethoxyphenyl)-2-piperidino-propan-1-ol had a melting point of 81° C to 83° C (8.5 g) and melted at 84° C to 85° C, after recrystallization from isopropanol.

EXAMPLE 10 (T 2259)

21 g of α-piperidino-propiophenone were added to a Grignard solution of 7.3 g of magnesium, 36.4 g of 2-bromo-4-tertiary-butylanisole, 28.2 g of 1,2-dibromoethane and 300 ml of diethyl ether. After boiling for 4 hours under reflux, the reaction mixture was poured onto ice and acidified with hydrochloric acid. The crystals, so precipitated, were filtered by suction, covered with a layer of diethyl ether and mixed with a concentrated aqueous ammonia solution until the crystals dissolved upon stirring or agitating. After evaporation of the diethyl ether, 33.3 g of a partly crystalline compound were obtained and dissolved in the necessary quantity of hot methanol. Upon cooling, 25.8 g of 1-(2'-methoxy-5'-tertiary-butylphenyl)-1-phenyl-2-piperidino-propan-1-ol having a melting point of 139° to 140° C crystallized out.

EXAMPLE 11 (T 2266)

10 g of 1-(4'-methoxy-3',5'-dimethyl)-2-piperidino-propan-1-ol were added to a Grignard solution of 4.8 g of magnesium, 27.1 g of 4-bromo-2,6-diisopropylanisole, 18.8 g of 1.2-dibromoethane and 200 ml of diethyl ether. After boiling for 4 hours under reflux, the reaction mixture was poured onto ice and acidified with hydrochloric acid. The precipitated crystals were filtered by suction, covered with a layer of diethyl ether and mixed with a concentrated aqueous ammonia solution until all the crystals have dissolved upon agitation. The diethyl ether extract was separated and dried over potash. After evaporation of the diethyl ether 16.0 g of a partly crystalline compound were obtained. After recrystallization from isopropanol 10.0 g of 1-(4'-methoxy-3',5'-diisopropylphenyl)-1-(4''-methoxy-3'',-5''-dimethylphenyl)-2-piperidinopropan-1-ol having a melting point of 118° to 119° C were obtained.

EXAMPLE 12 (T 2310)

12 g of p-methoxy-α-piperidino-propiophenone were added to a Grignard solution, of 6.1 g of magnesium, 35.7 g of 4-bromo-2,6-diisopropyl-phenetol, 23.5 g of 1,2-dibromo ethane and 200 ml of diethyl ether. After boiling for 4 hours under reflux, the reaction mixture was poured onto ice and acidified with hydrochloric acid. The aqueous acid solution and the oily intermediate layer were both separated together made alkaline with a concentrated aqueous ammonia solution and the precipitated base was dissolved in diethyl ether. After evaporation of the diethyl ether, 21.7 g of a brown oil was obtained which was dissolved in a small amount of isopropanol and then immediately acidified with aqueous 70% perchloric acid. Upon dilution, 18.9 g of 1-(4'-ethoxy-3',5'-diisopropylphenyl)-1-(4''-methoxyphenyl)-2-piperidino-propan-1-ol-perchlorate precipitated which, after recrystallization from isopropanol, melted at 147° C to 148° C.

EXAMPLE 13 (T 2350)

10 g of α-pyrrolidino-propiophenone were added to a Grinard solution of 7.3 g of magnesium, 41.5 g of 4-chloro-6-bromo-thymolmethylether, 28.2 g of 1,2-dibromoethane and 300 ml of diethyl ether. After boiling for 6 hours under reflux, the reaction mixture was poured onto ice and acidified with hydrochloric acid. The precipitated crystals were filtered by suction, covered with a layer of diethyl ether and mixed with a concentrated aqueous ammonia solution until they dissolved upon agitiation. The diethyl ether extract was separated and dried with potash. after evaporation of the diethyl ether 11.1 g of 1-(3'-chlor-6'-methoxy-2'-methyl-5'-isopropylphenyl)-1-phenyl-2-pyrrolidino-propan-1-ol having a crude m.p. of 108° to 109° C. After recrystallization from methanol the pure compound melted at 112° C to 113° C.

EXAMPLE 14 (T 2378)

12 g of p-methoxy-60-piperidino-propiophenone were added to a Grignard solution of 12.2 g of magnesium, 80.0 g of 2-(2',3'-dibromopropyl)-4,5-methylenedioxy-bromobenzene, 18.8 g of 1,2-dibromoethane and 300 ml of diethyl ether. After boiling for 6 hours under reflux, the reaction mixture was poured onto ice and acidified with hydrochloric acid. After a certain amount of time the precipitated dark oil partially crystallized. The crystals were filtered by suction, washed with diethyl ether and subsequently decomposed with a concentrated aqueous ammonia solution. The free base was dissolved in diethyl ether and diethyl ether extract was dried over potash. After evaporation of the diethyl ether, 4.8 g 1-(3',4'-methylene dioxy-6'-allylphenyl)-1-

(4″-methoxyphenyl)-2-piperidino-propan-1-ol, having a crude melting point of 117° to 130° C, were obtained. After treatment with activated carbon and recrystallization from isopropanol the pure compound had a melting point o 132° to 133.5° C.

EXAMPLE 15 (T 2435)

10 g of p-ethoxy-α-piperidino-propiophenone, dissolved in 100 ml of diethyl ether, were added to a Grignard solution of 7.3 g of magnesium, 42.8 g of 4-bromo-2,6-diisopropyl phenetol and 28.2 g of 1,2-dibromoethane in 100 ml of diethyl ether. After boiling for 4 hours under reflux, the reaction mixture was poured onto ice and the mixture acidified with hydrochloric acid. The oily intermediate layer and the aqueous acidic layer were both separated, together made alkaline with a concentrated aqueous ammonia solution and the base which precipitated therefrom was dissolved in ether. After drying over potash and evaporation of the diethyl ether, a brown oil remained (23 g) which was dissolved in 20 ml of isopropanol. The solution was acidifid by drop-by-drop addition of aqueous 70 percent perchloric acid during which 17.4 g of 1-(4′-ethoxy-3′, 5′-diisopropylphenyl)-1-perchlorate having a melting point of 160° to 161° C (decomposition), crystallized out. After recrystallizaton from isopropanol the pure perchlorate melted at 161° to 162° C. The free base was liberated from the perchlorate with a dilute caustic soda solution dissolved in diethyl ether and dried over potash. After evaporation of the diethyl ether, 1-(4′-ethoxy-3′, 5′-diisopropylphenyl)-1-(4″-ethoxyphenyl)-2-piperidino-propan-1-ol was obtained as a colourless viscous oil (14.0 g). By adding a calculated quantity of aqueous hydrochloric acid, the free base could be converted into the corresponding hydrochloride which was chosen as the form for administration in the pharmacological tests.

EXAMPLE 16 (T 2455)

7 g of 2,4-dimethoxy-α-piperidino-propriophenone in 100 ml of diethyl ether were added to a Grignard solution of 7.3 g of magnesium, 38.6 g of 2-methoxy-3-methyl-5-tertiary-butyl-bromobenzene, 28.2 g of 1,2-dibromoethane and 200 ml of diethyl ether. After boiling for 6 hours under reflux, the reaction mixture was poured onto ice and acidified with hydrochloric acid. The diethyl ether layer was separated and discarded, whilst the aqueous acidic layer was made alkaline with a concentrated aqueous ammonia solution and was extracted several times with ether. The combined ether extracts were dried over potash and then the diethyl ether was evaporated. The residual brownish oil (13.4 g) crystallized on diluted with a little isopropanol. The pure 1-(2′-methoxy-3′-methyl-5′-tertiary-butylphenyl)-1-(2″, 4″-dimethoxyphenyl)-2-piperidino-propan-1-ol, having a melting point of 133.5° to 135° C, was obtained after two recrystallizations from about 200 ml of isopropaol in each case.

EXAMPLE 17 (T 2458)

5 g of 2-methoxy-4-hydroxy-(or 2-hydroxy-4-methoxy)-α-piperidinopropiophenone (obtained from 2,4-dimethoxypropiophenone, which is a by-product from the preliminary stage of the production 2,4-dimetoxy-α-piperidinopropiophenone) dissolved in 100 ml of ether were added to a Grignard solution of 7.3 g of magnesium, 38.6 g of 2-methoxy-3-methyl-5-tertiary-butyl-bromobenzene, 28.2 g of 1,2-dibromoethane and 150 ml diethyl ether. The reaction mixture was boiled for 4 hours under reflux, was then poured onto ice and acidifid with hydrochloric acid. The mixture was vigorously agitated and then the diethyl ether was separated. The separated ether layer was then thoroughly agitated several times with semi-concentrated hydrochloric acid. The combined aqueous, hydrochloric acid extracts were then covered with a layer of 200 ml of diethyl ether and a concentrated aqueous ammonia solution was then added dropwise thereto until the pH-value of the mixture reached 8. The diethyl ether layer was then separated, the aqueous alkaline solution was extracted several times with diethyl ether and the combined ether extracts of the ammoniacal solution were dried over sodium sulphate. After evaporation of the diethyl ether 14.5 g of a brown oil remained. On dilution with a little isopropanol the oil crystallized out. The crystals (5.2 g having a crude melting point of 146° to 148° C) were filtered by suction and recrystallized several times from isopropanol. The melting point of the pure 1(2′-methoxy-3′-methyl-5′-tertiary-butylphenyl)-1-(2″-methoxy-4″-hydroxyphenyl- (or 2″-hydroxy-4″-methoxyphenyl)-2-piperidino-propan-1-ol was then 153.5° to 155° C.

EXAMPLE 18 (T 2464)

7.0 g of 3,4-dimethoxy-α-piperidinopropiophenone, dissolved in 100 ml ether, were added to a Grignard solution of 7.3 g of magnesium, 38.6 g of 2-methyl-6-bromo-4-tertiary-butyl anisole 28.2 g of 1,2-dibromoethane and 100 ml diethyl ether. The reaction mixture was heated to boiling for 4 hours under reflux and then poured onto ice. After acidification with hydrochloric acid and after stirring, three layers were formed. The upper diethyl ether layer was separated and discarded, the lower, aqueous layer and the oily central layer together were covered with a layer of fresh diethyl ether and, subsequently, were made alkaline with a concentrated aqueous ammonia solution. The diethyl ether layer above the alkaline solution was separated, dried with potash and evaporated. 13.4 g of a light-brown oil remained, which was dissolved in 100 ml of hot methanol. Upon cooling 8.3 g of 1-(2′-methoxy-3′-methyl-5′-tertiary-butylphenyl)-1-(3″, 4″-dimethoxyphenyl)-2-piperidinopropan-1-ol, having a melting point of 125° to 126° C, crystallized out. The melting point of the pure compound, after treatment with activated carbon and two recrystallizations from methanol, was 127° to 128° C.

EXAMPLE 19 (T 2481)

6.0 g of 4-benzyloxy-3,5-diisopropyl-α-piperidino-propiophenone in 100 ml of diethyl ether were added to a Grignard solution of 7.3 g of magnesium, 30.2 g of 2-bromomethyl anisole, 28.2 g of 1,2-dibromoethane and 100 ml of diethyl ether. After boiling for 4 hours under reflux, the mixture was poured onto ice and acidified with hydrochloric acid. The resultant oily intermediate layer and the aqueous phase were both separated together mixed with diethyl ether and a concentratd aqueous ammonia solution and agitated thoroughly. The diethyl ether extract so obtained was separated, dried over potash and the ether evaporated. The residual brown oil (12.1 g) was dissolved in 40 ml of isopropanol and was acidified with saturated isopropanolic picric acid. 12.1 g of the picrate, having a crude melting point of 95° to 100° C, crystallized out. After recrystallization from isopropanol, the pure picrate melted at 99° to 101° C. The 1-(2'-methoxy-5'-methylphenyl)-1-(4''-benzyloxy-3'', 5''-diisopropylphenyl)-2-piperidino-propan-1-ol was obtained as a colourless oil by decomposition of the pure picrate with ethanolamine, in accordance with the directions of I.A. Kaye et al (J. Amer. Chem. Soc. 72, 5752 (1950). By adding a calculated amount of aqueous hydrochloric acid, the free base could be converted into the corresponding hydrochloride which was chosen as the form for administration in the pharmacological tests.

EXAMPLE 20 (T 2493)

5 g of 4-methoxy-3,5-dimethyl-α-(methyl-tertiary-butylamino)-propiophenone in 100 ml of ether were added to a Grignard solution of 7.3 g of magnesium, 35.3 g of 6-bromo-4-chloro-2-methylanisole, 28.2 g of 1,2-dibromoethane and 100 ml diethyl ether. The mixture was boiled for 4 hours under reflux. Subsequently, the mixture was poured onto ice and acidified with hydrochloric acid. The resultant mixture was thoroughly agitated in a separating funnel, the diethyl ether layer being separated and discarded. The aqueous layer and the oily intermediate layer together were rendered alkaline with an aqueous concentrated ammonia solution and were then extracted with diethyl ether. This diethyl ether extract was dried over potash and the ether was evaporated. 10.1 g of a brown alkaline oil remained which was dissolved in 20 ml of methanol and was mixed with a saturated methanolic picric acid solution until the solution reacted acidically over the crystals precipitated therefrom. The resultant crude 1-(6'-methoxy-5'-methyl-3'-chlorophenyl)-1-(4''-methoxy-3'', 5''-dimethylphenyl)-2-(methyl-tertiary-butylamino)-propan-1-ol-picrate (9.4 g) had a melting point of 179° to 180° C. The pure picrate, which melted at 185° to 186° C after two recrystallizatons from methanol, was decomposed with ethanolamine in accordance with the directions of I.A. Kaye et al (J. Amer. Chem. Soc. 72,5752 (1950)). The resultant colourless, oily 1-(3'-chloro-6'-methoxy-5'-methylphenyl)-1-(4''-methoxy-3'', 5''-dimethylphenyl)-2-(N-methyl-tertiary-butylamino)-propan-1-ol could be converted, by the addition of a calculated quantity of aqueous hydrochloric acid, into the correspondng hydrochloride which was chosen as the form for administration in the pharmacological tests.

We claim:

1. A pharmaceutical composition wherein the active ingredient is 1-(7', 8'-Dimethylchromanyl-(6'))-1-phenyl-2-piperidino-propan-1-ol, together with a pharmaceutically acceptable diluent or carrier.

2. 1-(7', 8'-Dimethylcromanyl-(6'))-1-phenyl-2-piperidino-propan-1-ol.

3. A pharmaceutical composition wherein the active ingredient is 1-(3', 4'-Methylene-dioxy-6'-allylphenyl)-1-(4''-methoxyphenyl)-2-piperidino-propan-1-ol, together with a pharmaceutically acceptable diluent or carrier.

4. 1-(3', 4'-Methylene dioxy-6'-allylphenyl-1-(4''-methoxyphenyl)-2-piperidino-propan-1-ol.

* * * * *

UNITED STATES PATENT OFFICE
CERTIFICATE OF CORRECTION

Patent No. 4,025,633  Dated May 24, 1977

Inventor(s) Wilhelm A. Behrendt et al

It is certified that error appears in the above-identified patent and that said Letters Patent are hereby corrected as shown below:

In the heading of the patent [30] should read as follows:

--[30] Foreign Application Priority Data

March 4, 1974   Germany.........P 24 10 284.9
February 26,1975 Germany........P 25 08 203.5--.

Signed and Sealed this second Day of August 1977

[SEAL]

Attest:

RUTH C. MASON
Attesting Officer

C. MARSHALL DANN
Commissioner of Patents and Trademarks